United States Patent [19]

Kim

[11] Patent Number: 5,780,479

[45] Date of Patent: Jul. 14, 1998

[54] USE OF OPIOID ANTAGONISTS TO TREAT IMPULSE-CONTROL DISORDERS

[75] Inventor: Suck Won Kim, Edina, Minn.

[73] Assignee: Regents of the University of Minnesota, Minneapolis, Minn.

[21] Appl. No.: 835,080

[22] Filed: Apr. 4, 1997

[51] Int. Cl.$^6$ .................................................. A61K 31/445
[52] U.S. Cl. .......................................... 514/282; 514/279
[58] Field of Search ................................... 514/282, 289, 514/279

[56] References Cited

U.S. PATENT DOCUMENTS

| | | | |
|---|---|---|---|
| 4,816,586 | 3/1989 | Portoghese | 544/340 |
| 5,086,058 | 2/1992 | Sinclair et al. | 514/282 |
| 5,298,622 | 3/1994 | Portoghese et al. | 546/15 |
| 5,411,965 | 5/1995 | Reid et al. | 514/279 |
| 5,457,208 | 10/1995 | Portoghese et al. | 546/35 |

OTHER PUBLICATIONS

"Impulse–Control Disorders Not Elsewhere Classified", *Diagnostic and Statistical Manual of Mental Disorders, Fourth Edithion*, American Psychiatric Association, Washington, D.C., 609–621 (1994).

Campbell, M., et al., "Naltrexone in Autistic Children: Behavioral Symptoms and Attentional Learning", *J. Am. Acad. of Child Adolesc. Psychiatry*, 32, 1283–1291 (Nov. 1993).

Carrion, V.G., "Naltrexone for the treatment of Trichotillomania: A Case Report", *J. Clin. Psychopharmacol.*, 15, 444–445 (Dec. 1995).

Cotton, R., et al., "ICI 174864: A Highly Selective Antagonist for the Opioid Delta–Receptor", *Eur. J. Pharmacol.*, 97, 331–332 (1984).

Froehlich, J.C., et al., "Importance of Delta Opioid Receptors in Maintaining High Alcohol Drinking", *Psychopharmacology*, 103, 467–472 (1991).

Froehlich, J.C., et al., "Naloxone Attenuates Voluntary Ethanol Intake in Rats Selectively Bred for Ethanol Preference", *Pharmacology Biochemistry and Behavior*, 35, 385–390 (1990).

Hollander, E., et al., "Obsessive Compulsive and Spectrum Disorders: Overview and Quality of Life Issues", *J. Clin. Psychiatry*, 57, S8, 3–6 (1996).

Insel, T.R., et al., "Naloxone Administration in Obsessive–Compulsive Disorder: Report of Two Cases", *Am. J. Psychiatry*, 140, 1219–1220 (Sep. 1983).

Jaffe, J.H., et al., "Opioid Analgesics and Antagonists", *The Pharmacological Basis of Therapeutics*, Gilman, A.G., et al., (eds.), Pergamon Press, New York, 485–521 (1990).

Jonas, J.M., et al., "The Use of Opiate Antagonists in Treating Bulimia: A Study of Low–Dose Versus High–Dose Naltrexone", *Psychiatry Research*, 24, 195–199 (1988).

Keuler, D.J., et al., "Behavioral Effects of Naloxone Infusion in Obsessive–Compulsive Disorder", *Biol. Psychiatry*, 40, 154–156 (1996).

Koob, G.F., et al., "Cellular and Molecular Mechanisms of Drug Dependence", *Science*, 242, 715–723 (4 Nov. 1988).

Kosten, T.R., et al., "Role of Opioid Antagonists in Treating Intravenous Cocaine Abuse", *Life Sciences*, 44, 887–892 (1989).

Martin, W.R., "Pharmacology of Opioids", *Pharmacological Reviews*, 35, 283–323 (1984).

McElroy, S.L., et al., "Clinical and Theoretical Implications of a Possible Link Between Obsessive–Compulsive and Impulse Control Disorders", *Depression*, 1, 121–132, (1993).

Roth, A.S., et al., "Naltrexone as a Treatment for Repetitive Self–Injurious Behavior: An Open–Label Trial", *J. Clin. Psychiatry*, 57, 233–237 (1996).

Sandyk, R., "Naloxone Abolishes Obsessive–Compulsive Behavior in Tourette's Syndrome", *Intern. J. Neuroscience*, 35, 93–94 (1987).

Shaw, J.S., et al., "Selective Antagonists at the Opiate Delta–Receptor", *Life Sciences*, 31, 1259–1262 (1982).

Sofuoglu, M., et al., "Differential Antagonism of Delta Opioid Agonists by Naltrindole and Its Benzofuran Analog (NTB) in Mice: Evidence for Delta Opioid Receptor Subtypes", *J. Pharmacol. and Exper. Therapeutics*, 257, 676–680 (1991).

Stein, D.J., et al., "Trichotillomania and Obsessive–Compulsive Disorder", *J. Clin. Psychiatry*, 56, S4, 28–35 (1995).

Swedo, S.E., et al., "Trichotillomania: An Obsessive–Compulsive Spectrum Disorder?", *Obsessional Disorders*, 15, 777–790 (Dec. 1992).

Volpicelli, J.R., et al., "Effect of Naltrexone on Alcohol High in Alcholics", *Am. J. Psychiatry*, 152, 613–615, (1995).

Volpicelli, J.R., et al., "Naltrexone in the Treatment of Alcohol Dependence", *Arch. Gen. Psychiatry*, 49, 876–880, (Nov. 1992).

Volpicelli, J.R., et al., "Naltrexone in the Treatment of Alcoholism: Predicting Response to Naltrexone", *J. Clin. Psychiatry*, S7, 39–44 (1995).

Willemsen–Swinkels, S.H., et al., "Failure of Naltrexone Hydrochloride to Reduce Self–Injurious and Autistic Behavior in Mentally Retarded Adults. Double–Blind Placebo–Controlled Studies", *Arch. Gen. Psychiatry*, 52, 766–773 (Sep. 1995).

Christenson et al., *CNS Drugs*, 6(1), 24–34 (1996).

*Primary Examiner*—Phyllis G. Spivack
*Attorney, Agent, or Firm*—Schwegman, Lundberg, Woesnner & Kluth, P.A.

[57] ABSTRACT

A method is provided for treating an individual afflicted with an impulse-control disorder by administering thereto an amount of one or more opioid receptor antagonists.

31 Claims, No Drawings

USE OF OPIOID ANTAGONISTS TO TREAT IMPULSE-CONTROL DISORDERS

BACKGROUND OF THE INVENTION

Intermittent explosive disorder, kleptomania, pyromania, pathological gambling, and trichotillomania can be grouped as impulse-control disorders. However, commentators have recently questioned whether or not trichotillomania is properly classified as an impulse-control disorder, and some have urged that it should be classified as an obsessive-compulsive disorder (OCD). See for example, V. G. Carrion, *J. Clin. Psychopharmacol*, 15 444 (1995); D. J. Stern et al., *J. Clin. Psychiatry*, 56, (suppl. 4) 28 (1995) and S. E. Swedo et al., *Psychiatr. Clin. North Am.*, 15, 777 (1992). Compulsive shopping and the other descriptive diagnoses describe problematic behaviors that are triggered by uncontrollable underlying urges. Urges, however, have not been defined as the primary problem. Instead, they have been viewed as one of the symptoms of each disorder.

Endogenous opioid peptides are involved in the mediation or modulation of a variety of physiological processes, many of which are mimicked by opiates or other non-endogenous opioid ligands. Some of the effects that have been investigated are analgesia, tolerance and dependence, appetite, renal function, gastrointestinal motility, gastric secretion, learning and memory, mental illness, epileptic seizures and other neurobiological disorders, cardiovascular responses and respiratory depression.

The fact that the effects of endogenous and exogenous opioids are mediated by at least three different types, mu (µ), delta (δ), kappa (κ), of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side effects mediated through other opioid receptor types can be minimized or eliminated.

The prototypical opioid antagonists, naloxone and naltrexone, are used primarily as pharmacologic research tools and for the reversal of toxic effects of opioids in case of overdose. Since these antagonists act at multiple opioid receptors, their application in other therapeutic areas or as pharmacologic tools would appear to be limited. Nevertheless, the efficacy of naltrexone has been tested in bulimia nervosa (J. M. Jonas et al., *Psych. Res.*, 24, 195 (1987)), alcoholism (J. R. Volpicelli et al., *Arch. Gen. Psych.*, 49 876 (1992)), borderline personality disorder with self-injurious behavior (A. S. Roth et al., *J. Clin. Psychiatry*, 57, 233 (1996)), drug abuse (T. R. Kosen et al., *Life Sciences*, 44, 887 (1989)), obsessive-compulsive disorder (OCD) (R. Sandyk, *Int. J. Neurosci.* 35 93 (1987)), mental retardation with self-injurious behavior (S. H. Willemsen-Swinkels, *Arch. Gen. Psychiatry*, 52, 766 (1995)), and other psychiatric disorders (M. Campbell et al., *J. Amer. Acad. Child Adolescent Psych.*, 32, 1283 (1993)). Both positive and negative efficacy data have been reported except in alcoholism in which the efficacy has been established (J. R. Volpicelli et al., *J. Clin. Psychiatry*, 7 (suppl.), 39 (1995)). Overall impression within the research and clinical community is that naltrexone is not highly effective in most of these disorders. The opioid receptor antagonist naloxone, has been reported to suppress ethanol, but not water intake, in a rat model of alcoholism (J. C. Froehlich et al., *Pharm. Biochem. Behav.*, 35, 385 (1990)).

Some progress has been made in the development of highly selective opioid antagonists. For example, Portoghese et al. (U.S. Pat. No. 4,816,586) disclose certain opiate analogs, including naltrindole (NTI), which possess high selectivity and potency at delta receptors. Minimal involvement was observed at mu and kappa opioid receptors. NTI has been disclosed to inhibit the reinforcing effects of cocaine in animal models (Reid et al., U.S. Pat. No. 5,411,965) and to block morphine tolerance and dependence in the rat model (M. Sofuoglu et al., *J. Pharmacol. Exp. Ther.*, 257, 676 (1991)).

Historically, impulse-control disorders (ICD) have been considered refractory to known pharmacological or psychotherapeutic treatments. Therefore, a continuing need exists for agents which will be effective to treat (eliminate or reduce) these symptoms associated with ICD's.

SUMMARY OF THE INVENTION

The present invention provides a therapeutic method comprising administering an amount of at least one opioid receptor antagonist to an individual afflicted with an impulse-control disorder, which amount is effective to treat (eliminate or reduce) at least one of the symptoms of said impulse-control disorder.

As used herein, the term "impulse-control disorder" (ICD) includes intermittent explosive disorder, kleptomania, pyromania, pathological gambling and compulsive shopping. As discussed above, and as used hereinbelow, the term ICD does not include trichotillomania. These disorders are well-characterized and diagnosable by the art, as discussed hereinbelow.

As used herein, the term "opioid receptor antagonist" includes both pure and mixed opioid receptor antagonists, as defined in *Goodman and Gilman's The Pharmacological Basis of Therapeutics*, Pergamon Press, NY at pages 487–489. Antagonists that bind with high specificity to µ, δ or κ receptors are included within the term, such as NTI, as are relatively nonspecific antagonists, such as naltrexone and naloxone.

The term "at least one" as used herein with respect to opioid receptor antagonists means that the antagonists can be used singly or in combination to achieve the desired effect, i.e., 1–3 or more antagonists may be delivered in one or a plurality of unit dosage forms.

DETAILED DESCRIPTION OF THE INVENTION

1. Intermittent Explosive Disorder

The essential feature of Intermittent Explosive Disorder is the occurrence of discrete episodes of failure to resist aggressive impulses that result in serious assaultive acts or destruction of property. The degree of aggressiveness expressed during an episode is grossly out of proportion to any provocation or precipitating psychosocial stressor. A diagnosis of Intermittent Explosive Disorder is made only after other mental disorders that might account for episodes of aggressive behavior have been ruled out (e.g., Antisocial Personality Disorder, Borderline Personality Disorder, a Psychotic Disorder, a Manic Episode, Conduct Disorder, or Attention Deficit/Hyperactivity Disorder). The aggressive episodes are not due to the direct physiological effects of a substance (e.g., an abused drug, a medication) or a general medical condition (e.g., head trauma, Alzheimer's disease). The individual may describe the aggressive episodes as "spells" or "attacks" in which the explosive behavior is preceded by a sense of tension or arousal and is followed immediately by a sense of relief Later the individual may feel upset, remorseful, regretful, or embarrassed about the aggressive behavior.

2. Kleptomania

The essential feature of Kleptomania is the recurrent failure to resist impulses to steal items even though the items are not needed for personal use or for their monetary value. The individual experiences a rising subjective sense of tension before the theft and feels pleasure, gratification, or relief when committing the theft. The stealing is not committed to express anger or vengeance, is not done in response to a delusion or hallucination, and is not better accounted for by Conduct Disorder, a Manic Episode, or Antisocial Personality Disorder. The objects are stolen despite the fact that they are typically of little value to the individual, who could have afforded to pay for them and often gives them away or discards them. Occasionally the individual may hoard the stolen objects or surreptitiously return them. Although individuals with this disorder will generally avoid stealing when immediate arrest is probable (e.g., in full view of a police officer), they usually do not preplan the thefts or fully take into account the chances of apprehension. The stealing is done without assistance from, or collaboration with, others.

3. Pyromania

The essential feature of Pyromania is the presence of multiple episodes of deliberate and purposeful fire setting. Individuals with this disorder experience tension or affective arousal before setting a fire. There is a fascination with, interest in, curiosity about, or attraction to fire and its situational contexts (e.g., paraphernalia, uses, consequences). Individuals with this disorder are often regular "watchers" at fires in their neighborhoods, may set off false alarms, and derive pleasure from institutions, equipment, and personnel associated with fire. They may spend time at the local fire department, set fires to be affiliated with the fire department, or even become firefighters. Individuals with this disorder experience pleasure, gratification, or a release of tension when setting the fire, witnessing its effects, or participating in its aftermath. The fire setting is not done for monetary gain, as an expression of sociopolitical ideology, to conceal criminal activity, to express anger or vengeance, to improve one's living circumstances, or in response to a delusion or a hallucination. The fire setting does not result from impaired judgment (e.g., in dementia, Mental Retardation, or Substance Intoxication).

4. Pathological Gambling

The essential feature of Pathological Gambling is persistent and recurrent maladaptive gambling behavior that disrupts personal, family, or vocational pursuits. The diagnosis is not made if the gambling behavior is better accounted for by a Manic Episode.

The individual may be preoccupied with gambling (e.g., reliving past gambling experiences, planning the next gambling venture, or thinking of ways to get money with which to gamble). Most individuals with Pathological Gambling say that they are seeking "action" (an aroused, euphoric state) even more than money. Increasingly larger bets, or greater risks, may be needed to continue to produce the desired level of excitement. Individuals with Pathological Gambling often continue to gamble despite repeated efforts to control, cut back, or stop the behavior. There may be restlessness or irritability when attempting to cut down or stop gambling. The individual may gamble as a way of escaping from problems or to relieve a dysphoric mood (e.g., feelings of helplessness, guilt, anxiety, depression). A pattern of "chasing" one's losses may develop, with an urgent need to keep gambling (often with larger bets or the taking of greater risks) to undo a loss or series of losses. The individual may abandon his or her gambling strategy and try to win back losses all at once. Although all gamblers may chase for short periods, it is the long-term chase that is more characteristic of individuals with Pathological Gambling. The individual may lie to family members, therapists, or others to conceal the extent of involvement with gambling. When the individual's borrowing resources are strained, the person may resort to antisocial behavior (e.g., forgery, fraud, theft, or embezzlement) to obtain money. The individual may have jeopardized or lost a significant relationship, job, or educational or career opportunity because of gambling. The individual may also engage in "bailout" behavior, turning to family or others for help with a desperate financial situation that was caused by gambling.

The diagnoses discussed hereinabove are excerpted from the *Diagnostic and Statistical Manual of Mental Disorders*, American Pyschiatric Association, Washington D.C. (4th ed. 1994) at 609–621. Compulsive shopping shares many of the features of pathological gambling, as discussed in Ex. 2 below.

Preferred opioid antagonists for use in the present method include those of formula (I):

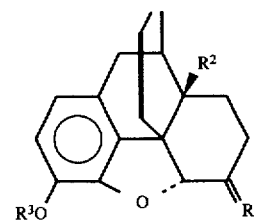

wherein $R^1$ is $(C_3-C_4)$cycloalkylmethyl, or allyl, $R^2$ is H or OH, $R^3$ is H or $(C_1-C_4)$alkyl, R is O, $CH_2$ or $(H)_2$, or a pharmaceutically acceptable salt thereof. This group of morphinan derivatives includes those depicted in Table I below:

TABLE I

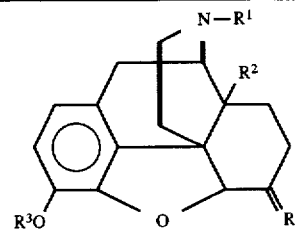

| $R^1$ | $R^2$ | $R^3$ | R | Common Name | Merck No.[1] |
|---|---|---|---|---|---|
| $CH_2CH(CH_2)_2$ | OH | H | O | naltrexone | 6278 |
| $CH_2CH=CH_2$ | OH | H | O | naloxone | 6277 |
| $CH_2CH(CH_2)_2$ | OH | H | $CH_2$ | nalmefene | 6274 |
| $CH_2CH=CH_2$ | H | H | $(H)_2$ | levallorphan | 5342 |

[1] The Merck Index, Merck & Co., Rahway, NJ (11th ed., 1989).

Another useful group of delta-specific antagonists includes the compounds of formula (II):

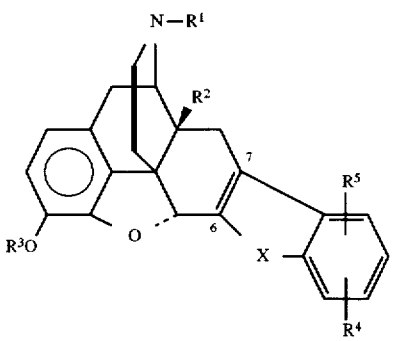

(II)

wherein $R^1$ is ($C_1$–$C_5$)alkyl, $C_3$–$C_6$(cycloalkyl)alkyl, $C_5$-$C_7$- (cycloalkenyl)alkyl, aryl, aralkyl, trans($C_4$–$C_5$)alkenyl, allyl or furan-2-ylalkyl, $R^2$ is H, OH or $O_2C(C_1$–$C_5$)alkyl; $R^3$ is H, ($C_1$–$C_5$)alkyl or ($C_1$–$C_5$)alkylCO; X is O, S or NY, wherein Y is H, phenyl, benzyl or ($C_1$–$C_5$)alkyl; and $R^4$ and $R^5$ are individually H, F, Cl, Br, $NO_2$, $NH_2$, ($C_1$–$C_5$)alkyl, ($C_1$–$C_5$)alkoxy or together are benzo; and the pharmaceutically acceptable salts thereof. The synthesis of these compounds is set forth in U.S. Pat. No. 4,816,586. NTI is the compound of formula (II) wherein $R^1$ is cyclopropylmethyl, $R^2$ is OH, $R^3$–$R^5$ are H and X is NH.

Delta-, mu- or mixed delta-, mu- antagonists that may be useful in the present invention are disclosed in U.S. Pat. No. 5,298,622. Kappa opioid receptor-specific NTI derivatives are disclosed in U.S. Pat. No. 5,457,208.

Other opioid receptor antagonists, including mixed agonist-antagonists, useful in the practice of the present invention include (followed by their Merck Index No.), cyclazocine (2710), nadide (6259), amphenazole, butorphenol, diprenorphine, etazocine, levallorphan (5342), nalbuphine, nalorphine (6275), pentazocine, cyprenorphine (2777), 7-benzylidenenaltrexone and buprenorphine.

Pentapeptides structurally related to the enkephalins have been reported to be highly delta-selective opioid antagonists. Such compounds (e.g., ICI 174864) currently are employed as pharmacologic tools, but they can possess the disadvantage of transient activity and poor penetration into the central nervous system (CNS). See J. W. Shaw et al., *Life Sci.*, 31, 1259 (1982) and R. Cotton et al., *Eur. J. Pharmacol.*, 97, 331 (1984). However, suppression of ethanol ingestion may be mediated by the delta opioid receptor subtype. For example, the established δ antagonist, N,N-diallyl-Tyr-Aib-Aib-Phe-Leu-OH (ICI 174864), strongly inhibits ethanol drinking, but has a very short duration of action, which may limit its clinical utility in the present method. See J. C. Froehlich et al., *Psychopharmacol.*, 103, 467 (1991).

Although the free-base form of the antagonists can be used in the methods of the present invention, it is preferred to prepare and use a pharmaceutically acceptable salt thereof. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, propriolate, propionate, phenylpropionate, salicylate, sebacate, succinate, suberate, sulfate, bisulfate, pyrosulate, sulfite, bisulfite, sulfonate, benzenesulfonate, p-bromophenylsulfonate, chlorobenzenesulfonate, ethanesulfonate, 2-hydroxyethanesulfonate, methanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

The pharmaceutically acceptable acid addition salts are typically formed by reacting the free base with an equimolar or excess amount of acid. The reactants are generally combined in a mutual solvent such as diethyl ether or benzene. The salt normally precipitates out of solution within about one hour to 10 days and can be isolated by filtration or the solvent can be removed by conventional means.

The organic acids can also be used to form nontoxic esters of the free hydroxyl groups present on the antagonist. For example, the mono- or dinicotinates or the 3-beta-D-glucuronide esters of nalmefene, nalorphine, naltrexone and naloxone can be prepared by methods known to the art. Ester can be formed by reacting the OH group or groups with an activated form of the acid, such as the acid chloride or anhydride.

The pharmaceutically acceptable salts generally have enhanced solubility characteristics compared to the compound from which they are derived, and thus are often more amenable to formulation as liquids or emulsions.

The compounds useful in the present method can be administered by a variety of routes including oral, rectal, transdermal, subcutaneous, intravenous, intramuscular, and intranasal. These compounds preferably are formulated prior to administration, the selection of which will be decided by the attending physician. Typically, one or more antagonists, or pharmaceutically acceptable salts or esters thereof, is combined with a pharmaceutically acceptable carrier, diluent or excipient to form a pharmaceutical formulation, or unit dosage form.

The total active ingredients in such formulations comprise from 0.1% to 99.9% by weight of the formulation. By "pharmaceutically acceptable" it is meant that the carrier, diluent, excipients, and/or salt must be compatible with the other ingredients of the formulation, and not deleterious to the recipient thereof.

Pharmaceutical formulations containing the antagonist or antagonists can be prepared by procedures known in the art using well-known and readily available ingredients. For example, the antagonist can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginate, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols.

The compounds also can be formulated as tablets or in capsules or as elixirs or solutions for convenient oral administration or as solutions appropriate for parenteral administration, for example, by intramuscular, subcutaneous or intravenous routes.

Additionally, the compounds are well suited to formulation as sustained or controlled release dosage forms. The formulations can be so constituted that they release the active ingredient only or preferably in a particular physiological location, optionally over a period of time. The coatings, envelopes, and protective matrices may be made, for example, from polymeric substances such as collagen or silicone, or from waxes. The compounds can also be delivered via patches for transdermal delivery, s.c. implants, infusion pumps or release from implanted depot sustained release dosage forms.

As used herein, the term "effective amount" means an amount of compound which is capable of inhibiting at least one of the symptoms of the ICDs herein described. The specific dose of a compound administered according to this invention will, of course, be determined by the particular circumstances surrounding the case including, for example, the compound administered, the route of administration, the condition of the patient, and the severity of the symptoms being treated. A typical daily dose will contain a nontoxic dosage level of from about 0.25 mg to about 500 mg/day of an opioid receptor antagonist of the present invention. Preferred daily doses generally will be from about 1 mg to about 300 mg/day.

Since naltrexone and nalmefene have been evaluated clinically to assess its ability to inhibit ethanol consumption by alcoholic patients, effective dosages of the compounds of the present invention can be extrapolated from doses found to be effective in those studies, as well as from the dosages of NTI found to be effective to decrease cocaine use in the rat model. See, for example, Volpicelli et al., cited above, and U.S. Pat. No. 5,086,058. Of course, the clinically effective dosages in the human subjects as disclosed in the examples hereinbelow may readily be extrapolated to human patients of other ages and in other conditions. For example, results may be achieved with naltrexone HCl at 1.5–5 mg/kg/day. It is preferable that the dose of antagonist be up-titrated until the effect emerges or when the symptoms recur. In most cases the effect emerges in adults at 100–200 mg/day of naltrexone. Because of a wide margin of dose-response pattern, a flexible-instead of fixed-dose program should be employed until a minimum effective dose is established for each disorder.

The invention will be further described by reference to the following detailed examples.

EXAMPLE 1

Treatment of Pathological Gambling

A fifty-five year old man presented severe pathological gambling and hoarding symptoms. Patient had lost $50,000 during the past 3 years. At 50 mg/day naltrexone patient reported no change in his symptoms. As soon as the naltrexone dose was raised to 100 mg/day on his second visit the patient reported "My most serious problem was gambling. I was addicted to the lights and chatter and other noises of the casino. It helped me get out of myself. If I had money to gamble I would start mental play while I was driving to the casino. Once I parked the car this mental play took on a high fever. By the time I walked into the casino my breathing was real shallow and quick and I almost am trembling and shaking over the excitement created in my mind."

"Now the gambling and hoarding urges are lifted and I feel like I am a new man. All that mind play about gambling and hoarding and guilt and other emotional stresses are gone. I went up to collect payment on my land and it was given to me in cash. If it would have been two months ago, I would have burnt the tires of the car getting to Hinckley (Minnesota) Casino. Instead, because of naltrexone, I drove sensibly to the casino. I was about to test myself. I parked the car, took four or five steps to the casino, and noticed my mind was clear. I was not calculating and strategizing and breathing shallow. As I walked to the casino my excitement wasn't there. I entered the casino and I felt like I was in a grocery store. I walked passed many machines and didn't put in one coin. I didn't have the urge to put in the coins. I did not feel like I was tempted and warding off temptation. It's a miracle." The patient reported that he has not spent one dime for the past 5 months and auctioned off his hoarded junk. He now has two jobs and a savings account in a bank.

EXAMPLE 2

Treatment of Compulsive Shopping

A forty-six year old woman reported seven-year history of bulimia nervosa symptoms and five-year history of compulsive shopping. At the time of seeking treatment, compulsive shopping symptoms were her chief complaint. Shopping symptoms have ruined her financial condition. She had eleven binge/purge cycles/week suggesting that her bulimic symptoms were also severe. She had a long history of cocaine and narcotics abuse but managed to overcome her problem through a series of CD treatments.

Her beginning naltrexone dose was 50 mg/day. She developed diarrhea and nausea. These side effects subsided in one week. She did not report symptom improvement. At week two her naltrexone was raised to 100 mg/day. She tolerated this dose well. Her shopping symptoms decreased significantly at this time. She said she no longer was developing elaborate plans or routes to sales. Incidentally, her binge/purge cycles decreased from eleven per week to one per week initially and presently she no longer has binge/purge symptoms. She reported a substantial decrease in her urges to shop and binge. Liver function tests are normal.

EXAMPLE 3

Treatment of Kleptomania

A thirty-eight year old woman presented severe washing and hoarding symptoms. Her symptoms started during her high school period and have been refractory to treatments given by OCD drug and behavior specialists in and out of the state. She also had uncontrolled stealing behavior. Whenever her mother accompanied her to a shopping center the mother would witness the stealing behavior. The mother was afraid that her daughter might end up in jail eventually. Urges to steal toys and dolls did not change at 50 mg/day naltrexone. When the naltrexone dose was raised to 100 mg/day she began to report decreased stealing urges. Since her naltrexone dose was raised to 150 mg/day she has not had stealing urges. Her washing and hoarding symptoms have not changed. Liver function tests are normal.

Summary

The effect size is impressive and the effect emerges faster and more predictably than what might be expected from usual psychiatric treatments (except with antianxiety agents). These findings further suggest that the treatment effect in impulse-control disorders is sustained. Many of the patients discussed above have now maintained improvement for several months.

Because of the putative overlap between compulsive and impulsive disorders (OCD), as discussed, for example, by S. L. McElroy et al., *Depression*, 1, 121 (1993) and by E. Hollander et al., *J. Clin. Psychiatry*, 57 (Suppl. 8), 3 (1996), we wondered if naltrexone might not also have an effect in the treatment of obsessions; so far our effort has not been successful. Patients afflicted with obsessive-compulsive disorders often have strong urges but their urges may be secondary to the underlying obsessions. Furthermore, OCD urges are usually associated with aversive stimulus. Although the studies were limited in scope, others also have tested naltrexone in OCD and found no significant effects. For example, see T. R. Insel et al., *Am. J. Psychiatry*, 140, 1219 (1983) and I. J. Kessler et al., *Biol. Psychiatry*, 40, 154 (1996). Further evaluation is needed especially for the OCD patients who have strong urges. The presence of urge symptoms, especially urges associated with a positively reinforcing stimulus, seems to be critical for naltrexone to be effective. If and when an individual engages in an impulsive act, naltrexone seems to reduce subjective experience of pleasure. This finding is consistent with findings by alcoholism researchers but differs from drug addiction researchers who argue that pleasure and craving reflect an opposite end of chemical or cellular mechanisms (for example, a high or low dopamine level within the neural system). See, for example, G. F. Koob et al., *Science* 242, 715 (1988) and J. R. Volpicelli et al., *Amer. J. Psychiatry*, 152, 613 (1995).

All of the publications cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A therapeutic method of treating an impulse-control disorder, with the exception of trichotillomania, comprising administering to an individual afflicted with an impulse-control disorder an amount of at least one opioid receptor antagonist effective to reduce or eliminate at least one of the symptoms of the impulse-control disorder.

2. The therapeutic method of claim 1 wherein the impulse-control disorder is pathological gambling.

3. The therapeutic method of claim 1 wherein the impulse-control disorder is intermittent explosive disorder.

4. The therapeutic method of claim 1 wherein the impulse-control disorder is compulsive shopping.

5. The therapeutic method of claim 1 wherein the impulse-control disorder is pyromania.

6. The therapeutic method of claim 1 wherein the impulse-control disorder is kleptomania.

7. The therapeutic method of claim 1 wherein the antagonist is administered orally.

8. The therapeutic method of claim 1 wherein the antagonist is administered parenterally.

9. The therapeutic method of claim 8 wherein the antagonist is administered by injection or infusion.

10. The therapeutic method of claim 8 wherein the antagonist is administered by means of a controlled release dosage form.

11. The therapeutic method of claim 10 wherein the antagonist is administered by means of a transdermal patch.

12. The therapeutic method of claim 1 wherein the antagonist is administered by inhalation.

13. The method of claim 1 wherein the antagonist is mu receptor-specific.

14. The method of claim 1 wherein the antagonist is delta receptor-specific.

15. The method of claim 1 wherein the antagonist is kappa receptor-specific.

16. A therapeutic method of treating an impulse-control disorder, with the exception of trichotillomania, comprising administering to an individual afflicted with an impulse-control disorder an amount of an opioid receptor antagonist of formula (I):

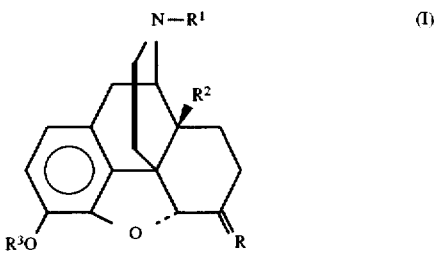

wherein $R^1$ is $(C_3-C_4)$cycloalkylmethyl or allyl, $R^2$ is H or OH, $R^3$ is H or $(C_1-C_4)$alkyl, R is O, $CH_2$ or $(H)_2$, or a pharmaceutically acceptable salt or ester thereof, effective to reduce or eliminate the symptoms of the impulse-control disorder.

17. The method of claim 16 wherein the compound of formula (I) is naltrexone.

18. The method of claim 16 wherein the compound of formula (I) is naloxone.

19. The method of claim 16 wherein the compound of formula (I) is nalmefene.

20. The method of claim 16 wherein the compound of formula (I) is levallorphan.

21. The therapeutic method of claim 16 wherein the impulse-control disorder is pathological gambling.

22. The therapeutic method of claim 16 wherein the impulse-control disorder is intermittent explosive disorder.

23. The therapeutic method of claim 16 wherein the impulse-control disorder is compulsive shopping.

24. The therapeutic method of claim 16 wherein the impulse-control disorder is pyromania.

25. The therapeutic method of claim 16 wherein the impulse-control disorder is kleptomania.

26. The therapeutic method of claim 16 wherein the antagonist is administered orally.

27. The therapeutic method of claim 16 wherein the antagonist is administered parenterally.

28. The therapeutic method of claim 27 wherein the antagonist is administered by injection or infusion.

29. The therapeutic method of claim 27 wherein the antagonist is administered by means of a controlled release dosage.

30. The therapeutic method of claim 29 wherein the antagonist is administered by means of a transdermal patch.

31. The therapeutic method of claim 16 wherein the antagonist is administered by inhalation.

* * * * *